United States Patent
Lee et al.

(10) Patent No.: US 9,701,613 B2
(45) Date of Patent: *Jul. 11, 2017

(54) PREPARATION METHOD OF 1-PALMITOYL-3-ACETYLGLYCEROL, AND PREPARATION METHOD OF 1-PALMITOYL-2-LINOLEOYL-3-ACETYLGLYCEROL USING SAME

(71) Applicant: ENZYCHEM LIFESCIENCES CORPORATION, Seoul (KR)

(72) Inventors: Tae-Suk Lee, Daejeon (KR); Jin-Soo Yook, Daejeon (KR); Chang-Hyun Yoo, Daejeon (KR); Cheol-Min Lee, Daejeon (KR); Eun-Kyung Kim, Nonsan-si (KR); Ju-Cheol Lee, Namyangju-si (KR)

(73) Assignee: ENZYCHEM LIFESCIENCES CORPORATION, Daejeon (KR)

( * ) Notice: Subject to any disclaimer, the term of this patent is extended or adjusted under 35 U.S.C. 154(b) by 31 days.

This patent is subject to a terminal disclaimer.

(21) Appl. No.: 14/958,734

(22) Filed: Dec. 3, 2015

(65) Prior Publication Data

US 2016/0083329 A1 Mar. 24, 2016

Related U.S. Application Data

(63) Continuation of application No. 14/346,783, filed as application No. PCT/KR2012/007644 on Sep. 24, 2012.

(30) Foreign Application Priority Data

Sep. 23, 2011 (KR) .................. 10-2011-0096341

(51) Int. Cl.
*C07C 59/245* (2006.01)
*C07C 59/90* (2006.01)
*C07C 67/08* (2006.01)
*C07B 57/00* (2006.01)
*C07C 67/14* (2006.01)
*C07C 69/30* (2006.01)

(52) U.S. Cl.
CPC .............. *C07C 67/08* (2013.01); *C07B 57/00* (2013.01); *C07C 67/14* (2013.01); *C07C 69/30* (2013.01)

(58) Field of Classification Search
CPC ........ C07C 51/00; C07C 59/245; C07C 59/90
USPC .................................. 554/151, 121
See application file for complete search history.

(56) References Cited

FOREIGN PATENT DOCUMENTS

| JP | 6094438 | 11/1994 |
|---|---|---|
| KR | 10-0283010 | 4/2001 |
| KR | 10-0291743 | 5/2001 |
| KR | 10-2006-0044536 | 5/2006 |
| KR | 10-2007-0010841 | 1/2007 |
| WO | WO 2005/090274 | 9/2005 |
| WO | WO 2007/011150 | 1/2007 |
| WO | WO 2013/043009 | 3/2013 |

OTHER PUBLICATIONS

Martin et al., Journal of the American Oil Chemists' Society, Dec. 1972, vol. 49, Issue 12, pp. 683-687.*
Burgos, et al.,"A new, asymmetric synthesis of lipids and phospholipids", J. Org. Chem., vol. 52 No. 22, (Oct. 1987) pp. 4973-4977.
Craven, et al., "Crystallization and Polymorphism of 1,3-Acyl-Palmitoyl-rac-Glycerols", J Am Oil Chem Soc, vol. 88, No. 8, (Feb. 2011), pp. 1113-1123.
Craven, et al., "Preparation of Diacid 1,3-Diacylglycerols", J Am Oil Chem Soc, vol. 87 No. 11, (Jun. 2010) pp. 1281-1291.
Han, et al., "Monoacetyldiglycerides as new Ca2+ mobilizing agents in rat pancreatic acinar cells" Bioorganic & Medicinal Chemistry Letters, vol. 9, (1999) pp. 59-64, Abstract Only.
Hwang, et al., "Highly Selective Asymmetric Synthesis of 2-Hydroxy Fatty Acid Methyl Esters Through Chiral Oxazolidinone Carboximides", JAOCS, vol. 9, No. 2, (Feb. 2001) pp. 205-211.
Martin, et al.,"Preparation and phase behavior of acetyl monoglycerides", Journal of the American Oil Chemists' Society, vol. 49, Issue 12, (1972), pp. 683-687, Abstract Only.
Written Opinion of the ISA (PCT/KR2012/007644), Feb. 22, 2013.

* cited by examiner

*Primary Examiner* — Yong Chu
*Assistant Examiner* — Sonya Wright
(74) *Attorney, Agent, or Firm* — Lex IP Meister, PLLC

(57) ABSTRACT

Disclosed are a method for preparing 1-palmitoyl-3-acetylglycerol in high purity and high yield without a purification process using a column chromatography, and a method for preparing 1-palmitoyl-2-linoleoyl-3-acetylglycerol in high purity and high yield using the same as a key intermediate. The method for preparing 1-palmitoyl-3-acetyl glycerol comprises the steps of: forming a reaction mixture including 1-palmitoyl-3-acetyl glycerol of the Formula 1 in the specification by reacting 1-palmitoylglycerol of the Formula 2 in the specification and an acetylating agent; and separating the optically active 1-palmitoyl-3-acetylglycerol by crystallizing the reaction mixture in a saturated hydrocarbon solvent having 5 to 7 carbon atoms.

17 Claims, No Drawings

PREPARATION METHOD OF 1-PALMITOYL-3-ACETYLGLYCEROL, AND PREPARATION METHOD OF 1-PALMITOYL-2-LINOLEOYL-3-ACETYLGLYCEROL USING SAME

REFERENCE TO RELATED APPLICATIONS

This application is a continuation application of U.S. patent application Ser. No. 14/346,783, filed Mar. 24, 2014, which is a U.S. National Phase Application of International Application No. PCT/KR2012/007644, filed Sep. 24, 2012, and claims priority to Korean Patent Application No. 10-2011-0096341, filed Sep. 23, 2011, the disclosures of each of these applications being incorporated herein by reference in their entireties.

FIELD OF THE INVENTION

This invention relates to a method for preparing 1-palmitoyl-3-acetylglycerol and a method for preparing 1-palmitoyl-2-linoleoyl-3-acetylglycerol using the same, and more specifically, to a method for preparing 1-palmitoyl-3-acetylglycerol in high purity and high yield without a purification process using a column chromatography, and a method for preparing 1-palmitoyl-2-linoleoyl-3-acetylglycerol in high purity and high yield using the 1-palmitoyl-3-acetylglycerol as a key intermediate.

BACKGROUND OF THE INVENTION

Rac-1-palmitoyl-2-linoleoyl-3-acetylglycerol is one of components of deer antler, and is known as one of the most active components having the growth-stimulating effects of hematopoietic stem cells and megakaryocytes which can be obtained from chloroform extracts of the deer antler (Korean Patent No. 10-0283010). In Korean Patent No. 10-0291743, two methods for preparing the rac-1-palmitoyl-2-linoleoyl-3-acetyl glycerol, (a) a method of synthesizing the compound from glycerol and (b) a method of using acetolysis of phosphatidylcholine are disclosed. However, the reaction of method (a) has no regioselectivity. Thus, from the reaction product of glycerol and palmitic acid, 1-palmitoylglycerol should be separated by using a column chromatography. The separated 1-palmitoylglycerol is acetylated and separated again by using a column chromatography. Then, a linoleoylation reaction is carried out for the above reaction product and a separation step using a column chromatography is again carried out to produce the target compound of rac-1-palmitoyl-2-linoleoyl-3-acetylglycerol. Since the reaction of method (a) has no regioselectivity, the reaction product of each reaction step should be separated and purified by using a column chromatography, and the overall yield of the target compound is very low (about 3.21% from glycerol). Furthermore, the reaction of method (a) utilizes Steglich esterification using N,N'-dicyclohexyl carbodiimide (DCC), and a side reaction, in which an acyl group is migrated in an adduct of DCC and carboxylic acid, may occur. To reduce the side reaction, the expensive catalyst 4-dimethylaminopyridine (DMAP) should be used in the amount of more than one equivalent. However, the side reaction cannot be completely suppressed, dicyclohexylurea is formed as a by-product, and it is difficult to completely remove the by-product by a filtration and an extraction.

In order to regioselectively synthesize glycerol derivative having ester groups of different fatty acids at 1 and 2-positions of glycerol and having acetyl group at 3-position of glycerol, the following process is generally carried out. First, an ester group is regioselectively introduced into 1-position of glycerol. Then, after protecting hydroxyl group of 3-position of glycerol which is more reactive than hydroxyl group of 2-position of glycerol, and ester group should be introduced into 2-position of glycerol. The process can regioselectively introduce ester groups into 1, 2 and 3-positions of glycerol. However, when removing the protecting group at 3-position of glycerol to introduce an ester group to the 3-position, there is a problem that the ester group of 2-position of glycerol is migrated to the 3-position of glycerol (J. Org. Chem., 52 (22), 4973~4977, 1987). Also, this method has drawbacks in that a protecting group should be introduced and the protecting group should be removed by which the overall reaction requires several reaction steps.

However, when a glycerol derivative having an ester group of fatty acid at 1-position of glycerol and acetyl group at 3-position of glycerol, for example, 1-palmitoyl-3-acetyl glycerol represented by the following Formula 1 is used to synthesis 1-palmitoyl-2-linoleoyl-3-acetylglycerol, the above-mentioned drawbacks can be eliminated. Therefore, there are demands for preparing racemic or optically active and pure 1-palmitoyl-3-acetylglycerol.

[Formula 1]

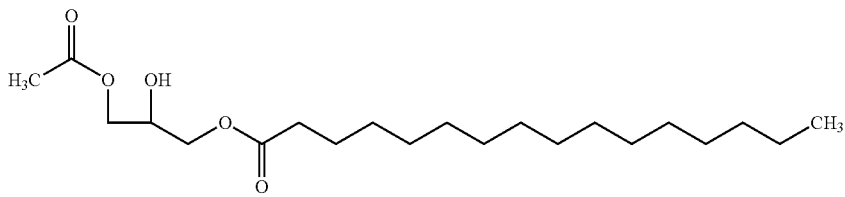

SUMMARY OF THE INVENTION

Accordingly, it is an object of this invention to provide a novel method for preparing racemic or optically active 1-palmitoyl-3-acetylglycerol in high purity and high yield without a separation and purification process using a column chromatography.

It is other object of this invention to provide a novel method for preparing racemic or optically active 1-palmitoyl-2-linoleoyl-3-acetylglycerol in high purity and high yield using 1-palmitoyl-3-acetylglycerol as an intermediate without a separation and purification process using a column chromatography.

To achieve the above-mentioned objects, this invention provides a method for preparing 1-palmitoyl-3-acetylglycerol comprising the steps of:

forming a reaction mixture including 1-palmitoyl-3-acetylglycerol represented by the following Formula 1 by reacting 1-palmitoylglycerol represented by the following Formula 2 and an acetylating agent; and separating optically active 1-palmitoyl-3-acetylglycerol by crystallizing the reaction mixture in a saturated hydrocarbon solvent having 5 to 7 carbon atoms.

[Formula 1]

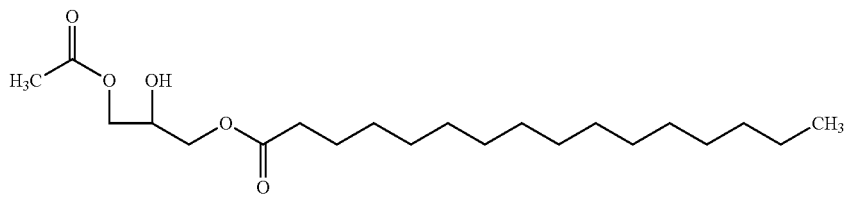

[Formula 2]

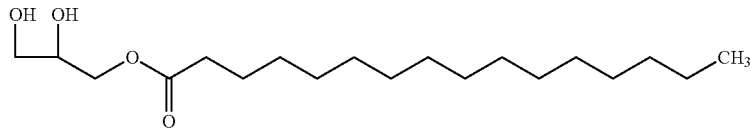

The compounds of the above formula 1 and 2 are racemic or optically active compounds.

This invention also provides a method for preparing 1-palmitoyl-2-linoleoyl-3-acetylglycerol comprising the steps of: preparing a mixed anhydride by reacting linoleic acid and pivaloyl chloride in a non-polar organic solvent in the presence of an organic base; and preparing 1-palmitoyl-2-linoleoyl-3-acetylglycerol represented by the following Formula 3 by reacting 1-palmitoyl-3-acetylglycerol and the mixed anhydride in the presence of 4-dimethylaminopyridine.

be prepared in high purity and high yield (more than 98%) by using 1-palmitoyl-3-acetylglycerol as an intermediate, and using pivaloyl chloride as a coupling reagent without the separation and purification process using a column chromatography. Accordingly, the methods of the present invention are suitable for a mass production.

A more complete appreciation of the invention, and many of the attendant advantages thereof, will be better appreciated by reference to the following detailed description.

By the method for preparing 1-palmitoyl-3-acetylglycerol and the method for preparing 1-palmitoyl-2-linoleoyl-3-

[Formula 3]

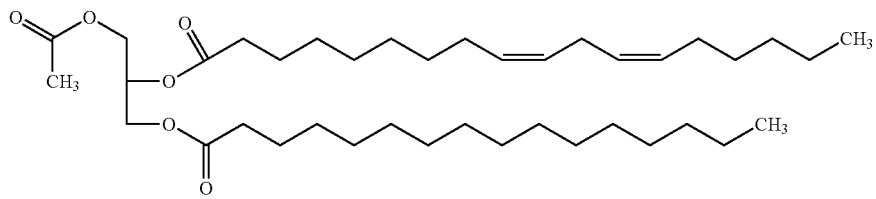

The compound of the above formula 3 is racemic or optically active compound.

DETAILED DESCRIPTION OF THE INVENTION

By the method for preparing 1-palmitoyl-3-acetylglycerol of the present invention, 1-palmitoyl-3-acetylglycerol (racemic or optically active compound) can be prepared in high purity and high yield by simple steps (an acetylation step and a crystallization step) without the separation and purification process using a column chromatography. Also, by the method for preparing 1-palmitoyl-2-linoleoyl-3-acetylglycerol of the present invention, 1-palmitoyl-2-linoleoyl-3-acetylglycerol (racemic or optically active compound) can acetylglycerol using the same according to the present invention, 1-palmitoyl-2-linoleoyl-3-acetylglycerol (racemic or optically active compound) and its intermediate 1-palmitoyl-3-acetylglycerol (racemic or optically active compound) are prepared in high purity and high yield without a separation and purification process using a column chromatography.

In order to prepare 1-palmitoyl-3-acetylglycerol of the following Formula 1 according to the present invention, first, a reaction mixture including the 1-palmitoyl-3-acetylglycerol is formed by reacting 1-palmitoylglycerol of the following Formula 2 and an acetylating agent as starting materials (acetylation reaction).

[Formula 1]

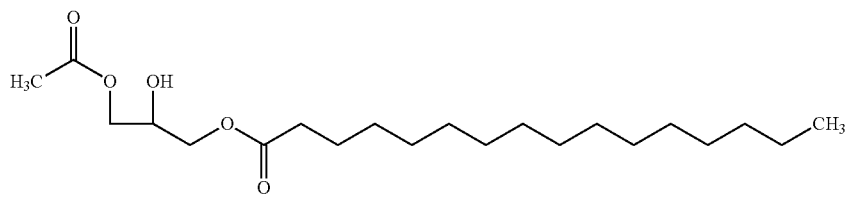

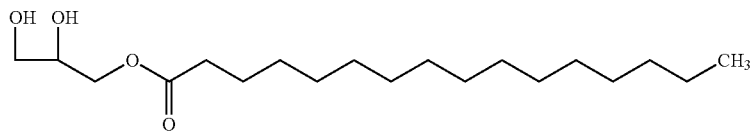

[Formula 2]

The compounds of the above formula 1 and 2 are racemic or optically active compounds.

When carrying out the acetylation reaction, besides 1-palmitoyl-3-acetylglycerol, 1-palmitoyl-2-acetylglycerol and 1-palmitoyl-2,3-diacetylglycerol are produced as by-products. From detailed study of reaction mechanisms, the inventors of the present invention have discovered that 1-palmitoyl-2-acetylglycerol is produced by competition reactions of hydroxyl groups at 2- and 3-positions of 1-palmitoylglycerol during the initial stage of the acetylation reaction, and the hydroxyl group at 3-position of the produced byproduct, 1-palmitoyl-2-acetylglycerol, is also acetylated in a competition reaction with the hydroxyl group at 3-position of the starting material, 1-palmitoylglycerol, to produce 1-palmitoyl-2,3-diacetylglycerol as the by-product.

Accordingly, the inventors of the present invention have tried to reduce the kind of compounds present in the reaction mixture after completion of the reaction by using the reaction mechanism. Specifically, the inventors has controlled the amount of the acetylating agent used in the acetylation reaction so that the by-product, 1-palmitoyl-2-acetylglycerol is completely converted to 1-palmitoyl-2,3-diacetylglycerol, and the starting material (1-palmitoylglycerol) does not exist, and thereby the reaction mixture includes only two compounds of 1-palmitoyl-3-acetylglycerol and the by-product of 1-palmitoyl-2,3-diacetylglycerol. In contrast, in a reaction of a conventional method, the reaction mixture includes 4 kind of compounds (1-palmitoyl-3-acetylglycerol, 1-palmitoyl-2-acetylglycerol, 1-palmitoyl-2,3-diacetylglycerol and unreacted 1-palmitoylglycerol). In the acetylation reaction of the present invention, it is very important to reduce the amounts of the starting material and the by-product of 1-palmitoyl-2-acetylglycerol. If they are remained in the reaction mixture, they are not removed during a purification process (a crystallization step) for purifying and obtaining pure 1-palmitoyl-3-acetylglycerol. Therefore, in finally synthesizing 1-palmitoyl-2-linoleoyl-3-acetylglycerol, by-products of 1-palmitoyl-2,3-linoleoyl-glycerol or 1-palmitoyl-2-acetyl-3-linoleoylglycerol can be produced. The by-products should be removed by using a column chromatography, which make the purification step very difficult.

Examples of the acetylating agent used in the present invention include acetylchloride, acetylbromide, the mixtures thereof and so on. The amount of the acetylating agent is 1.3 to 1.4 equivalents, preferably 1.31 to 1.35 equivalents with respect to the 1-palmitoylglycerol. When the amount of the acetylating agent is less than 1.3 equivalents with respect to the 1-palmitoylglycerol, the unreacted 1-palmitoylglycerol and 1-palmitoyl-2-acetylglycerol may be present in the reaction mixture. When the amount of the acetylating agent is more than 1.4 equivalents with respect to the 1-palmitoylglycerol, the produced 1-palmitoyl-3-acetylglycerol is further acetylated to produce 1-palmitoyl-2,3-acetylglycerol, which may reduce the yield of the 1-palmitoyl-3-acetylglycerol.

The acetylation reaction can be carried out in a solvent and in the presence of an organic base. Examples of the organic base include pyridine and so on. The amount of the organic base is 1.3 to 5 equivalents, preferably 2 to 4.5 equivalents, more preferably 3 to 4 equivalents with respect to 1-palmitoylglycerol. When the amount of the organic base is less than 1.3 equivalents with respect to 1-palmitoylglycerol, acids produced during the acetylation reaction may not be fully neutralized. When the amount of the organic base is more than 5 equivalents with respect to 1-palmitoylglycerol, there is no additional advantage. Examples of the solvent include a non-polar and aprotic solvent such as dichloromethane, acetone, ethyl acetate, the mixtures thereof, and so on, and preferably include dichloromethane. The amount of the solvent is 5 to 10 times, preferably 8 to 10 times in volume ratio with respect to the weight of 1-palmitoylglycerol (volume/weight). When the amount of the solvent is too small, the reaction mixture may not be smoothly stirred due to the salt precipitated during the reaction. When the amount of the solvent is too much, there is no additional advantage.

In the next step, the reaction mixture is crystallized in a saturated hydrocarbon solvent having 5 to 7 carbon atoms to separate 1-palmitoyl-3-acetylglycerol. When dissolving the reaction mixture including 1-palmitoyl-3-acetylglycerol and the by-product of 1-palmitoyl-2,3-diacetylglycerol in the saturated hydrocarbon solvent having 5 to 7 carbon atoms (for example, pentane, hexane, heptane, and so on, preferably, hexane), and cooling the mixture to a crystallization temperature of 0 to 15° C., preferably 5 to 10° C., 1-palmitoyl-2,3-diacetylglycerol having a high solubility to the solvent is remained dissolved, but 1-palmitoyl-3-acetylglycerol is crystallized out in pure form. The crystallized 1-palmitoyl-3-acetylglycerol is filtered to obtain 1-palmitoyl-3-acetylglycerol which is in a solid form at the room temperature with a relatively high yield (for example, 60 to 65%) and a high purity in a simple process. The obtained 1-palmitoyl-3-acetylglycerol does not includes impurities which produce by-products in the synthesis of 1-palmitoyl-2-linoleoyl-3-acetylglycerol. The amount of the saturated hydrocarbon solvent is 2.5 to 5 times, preferably 3 to 4 times in volume ratio with respect to the weight of the reaction mixture (volume/weight). When the amount of the saturated hydrocarbon solvent is too small, the reaction mixture may not be easily stirred in the crystallization process. When the amount of the saturated hydrocarbon solvent is too much, the yield of crystallized 1-palmitoyl-3-acetylglycerol may be decreased.

In order to prepare 1-palmitoyl-2-linoleoyl-3-acetylglycerol of the following Formula 3 according to the present invention, (a) 1-palmitoyl-3-acetylglycerol of the Formula 1 is prepared by the above-mentioned method for preparing 1-palmitoyl-3-acetylglycerol. (b) In the presence of an organic base, linoleic acid and pivaloyl chloride are reacted in a non-polar organic solvent to produce a mixed anhydride

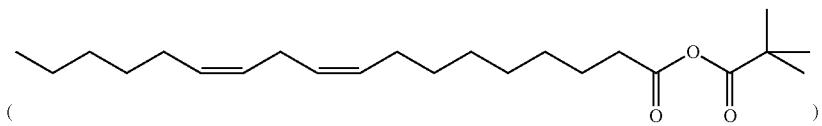 [SMILES: CCCCC/C=C\C/C=C\CCCCCCCC(=O)OC(=O)C(C)(C)C]

which is an active form of linoleic acid. (c) In the presence of 4-dimethylaminopyridine (DMAP), 1-palmitoyl-3-acetylglycerol of the Formula 1 and the mixed anhydride are reacted to produce 1-palmitoyl-2-linoleoyl-3-acetylglycerol of the following Formula 3.

[Formula 3]

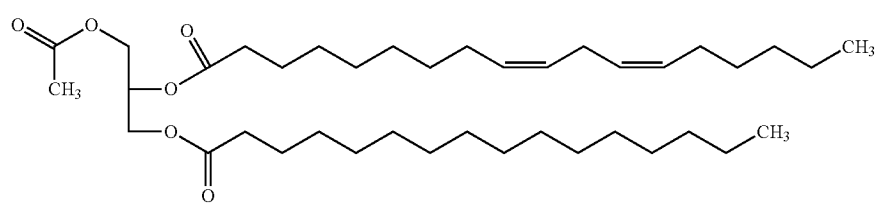

The compound of the above formula 3 is racemic or optically active compound.

The step of reacting linoleic acid and pivaloyl chloride (step (b)) can be easily carried out in a conventional non-polar organic solvent, but is preferably carried out in a saturated hydrocarbon solvent having 5 to 7 carbon atoms such as pentane, hexane, heptane, the mixtures thereof and so on in consideration of easy feasibility of product purification and possible residue of solvent in the product. The organic base is used to neutralize hydrochloric acid (HCl) produced in the reaction of linoleic acid and pivaloyl chloride and to neutralize pivalic acid produced in the reaction of the mixed anhydride and 1-palmitoyl-3-acetylglycerol. Examples of the organic base include triethylamine and so on.

In the step of reacting linoleic acid and pivaloyl chloride (step (b)), the amount of linoleic acid is 1 to 1.05 equivalents, preferably 1.01 to 1.04 equivalents with respect to 1-palmitoyl-3-acetylglycerol. The amount of pivaloyl chloride is less than or equal to the amount of linoleic acid. For example, the amount of pivaloyl chloride is 0.97 to 1 equivalents, preferably 0.98 to 0.99 equivalents with respect to linoleic acid. When the amount of linoleic acid is less than 1 equivalent with respect to 1-palmitoyl-3-acetylglycerol, there may be unreacted 1-palmitoyl-3-acetylglycerol when preparing 1-palmitoyl-2-linoleoyl-3-acetylglycerol. When the amount of linoleic acid is more than 1.05 equivalents with respect to 1-palmitoyl-3-acetylglycerol, there is no additional advantage and it may be difficult to remove the residual (unreacted) linoleic acid. When the amount of pivaloyl chloride is out of the above-mentioned range, pivaloyl chloride reacts with 1-palmitoyl-3-acetylglycerol to produce by-products or it may be difficult to remove the unreacted linoleic acid. The amount of the organic base is 2 to 3 equivalents, preferably 2.1 to 2.3 equivalents with respect to 1-palmitoylglycerol. When the amount of the organic base is out of the above-mentioned range, it may be difficult to neutralize hydrochloric acid (HCl) and pivalic acid produced in the reaction, and there is no additional advantage. The amount of the non-polar organic solvent is 10 to 15 times, preferably 11 to 12 times in volume ratio with respect to the weight of 1-palmitoyl-3-acetylglycerol (volume/weight). When the amount of the non-polar organic solvent is less than 10 times in volume ratio with respect to the weight of 1-palmitoyl-3-acetylglycerol, it may be difficult to stir the reaction mixture. When the amount of the non-polar organic solvent is more than 15 times in volume ratio with respect to the weight of 1-palmitoyl-3-acetylglycerol, there is no additional advantage.

The reaction of linoleic acid and pivaloyl chloride (step (b)) is carried out at the temperature of 15 to 25° C., preferably at the temperature of 20 to 24° C., and the reaction time is 30 to 60 minutes, preferably 40 to 50 minutes. When the reaction temperature and the reaction time are out of the above-mentioned ranges, the reaction may be slowly carried out or unreacted compounds may remain, and there is no additional advantage.

The step of reacting the mixed anhydride and 1-palmitoyl-3-acetylglycerol (step (c)) is carried out by: adding 1-palmitoyl-3-acetylglycerol and the catalyst 4-dimethyl aminopyridine (DMAP) to the reaction mixture including the mixed anhydride, and reacting the mixed anhydride and 1-palmitoyl-3-acetylglycerol at the temperature of 20 to 40° C., preferably 25 to 35° C. for 4 to 10 hours, preferably 5 to 6 hours. 1-palmitoyl-2-linoleoyl-3-acetylglycerol of Formula 3 prepared from the above-mentioned step can be obtained in high purity of more than 98% and in high yield of more than 70% by conducting simple purification process, for example, a conventional extraction process and adsorption process without conducting a purification process using a column chromatography.

The amount of 4-dimethylaminopyridine is 1 to 10 parts by mole, preferably 1.1 to 5 parts by mole with respect to 100 parts by mole of 1-palmitoyl-3-acetylglycerol. When the amount of 4-dimethylamino pyridine is less than 1 part by mole with respect to 100 parts by mole of 1-palmitoyl-3-acetylglycerol, the reaction may not be carried out or may be slowly carried out. When the amount of 4-dimethylamino pyridine is more than 10 parts by mole, there is no additional advantage. When the reaction temperature is less than 20° C., the reaction may be slowly carried out. When reaction temperature is more than 40° C., by-products may be produced and there is no advantage. Also, when the reaction time is less than 4 hours, the reaction may be incompletely carried out and unreacted compounds may remain. When the reaction time is more than 10 hours, there is no advantage.

Hereinafter, the preferable examples are provided for better understanding of the present invention. The following examples are provided only for illustrating the present invention, and the present invention is not limited by the following examples.

EXAMPLE 1

Preparation of rac-1-palmitoyl-3-acetylglycerol

Rac-1-palmitoylglycerol (250.0 g) was added into dichloromethane (2,500 ml), and pyridine (183.4 ml) is added thereto. Temperature of the reaction mixture is increased to 34 to 35° C. to completely dissolve rac-1-palmitoylglycerol, and the temperature is cooled to 25° C. again. Acetyl chloride (77.2 g) was slowly added to the reaction mixture at 20 to 25° C., and the reaction was carried out for 1 hour with stirring. After completion of the reaction, water (H2O, 1,250 ml) and concentrated hydrochloric acid (c-HCl, 125.8 ml) were added thereto to control the pH to about 2 to 3 and to induce a phase-separation. An organic layer is separated, and anhydrous magnesium sulfate (MgSO4, 28 g) was added to the organic layer, and stirred for 10 minutes. Next, magnesium sulfate was removed by a filtration, and the filtrate was concentrated at reduced pressure. Hexane (845 ml) was added to the residue, and the residue is cooled to 0 to 5° C. and stirred to precipitate a crystalline compound. After aging the crystalline compound for about 30 minutes, the crystalline compound is filtered and dried at 30° C. to obtain rac-1-palmitoyl-3-acetylglycerol (172.25 g). {Yield: 61%, mp: 42~43.5, 1H NMR (250 MHz, CDCl3): δ 0.88 (t, J=7.5 Hz, 3H), 1.16-1.25 (m, 24H), 1.62 (m, 2H), 2.06 (s, 3H), 2.37 (t, J=7.5 Hz, 2H), 2.43 (d, J=4.25 Hz, 1H), 4.03-4.21 (m, 5H)}.

EXAMPLE 2

Preparation of (R)-1-palmitoyl-3-acetylglycerol

Except for using (R)-1-palmitoylglycerol instead of rac-1-palmitoylglycerol, (R)-1-palmitoyl-3-acetylglycerol (170.14 g) was obtained in the same manner with Example 1 {Yield: 60%, mp: 37~37.5° C., [α]D=−0.83 (c=0.65, EtOH), 1H NMR (250 MHz, CDCl3): δ 0.88 (t, J=7.5 Hz, 3H), 1.17-1.25 (m, 24H), 1.62 (m, 2H), 2.07 (s, 3H), 2.37 (t, J=7.5 Hz, 2H), 2.43 (d, J=4.25 Hz, 1H), 4.03-4.22 (m, 5H)}.

EXAMPLE 3

Preparation of rac-1-palmitoyl-2-linoleoyl-3-acetylglycerol

Linoleic acid (99%, 2.89 g) and pivaloyl chloride (1.262 ml) were added to hexane (28.9 ml), and triethylamine (2.857 ml) was slowly added thereto at the solution temperature of 20 to 25° C. The reaction mixture was stirred for 30 minutes to produce a mixed anhydride. After adding rac-1-palmitoyl-3-acetylglycerol (3.726 g) prepared in Example 1 and 4-dimethylaminopyridine (DMAP, 61 mg) to the reaction mixture including the mixed anhydride, the reaction mixture is stirred for 6 hours at 25 to 35° C., and a purification process such as an extraction and an adsorption is carried out to obtain rac-1-palmitoyl-2-linoleoyl-3-acetylglycerol (4.63 g, Yield: 72.9%).

EXAMPLE 4

Preparation of (R)-1-palmitoyl-2-linoleoyl-3-acetylglycerol

Except for using (R)-1-palmitoyl-3-acetylglycerol prepared in Example 2 instead of rac-1-palmitoyl-3-acetylglycerol, (R)-1-palmitoyl-2-linoleoyl-3-acetylglycerol (4.47 g) was obtained in the same manner with Example 3 (yield: 70.39%).

What is claimed is:

1. A method of making 1-palmitoyl-3-acetylglycerol comprising the steps of:
   reacting 1-palmitoylglycerol with an acetylating agent, and
   separating the 1-palmitoyl-3-acetylglycerol thus formed by crystalization,
   wherein the 1-palmitoylglycerol and 1-palmitoyl-3-acetylglycerol are racemic or optically active compounds and wherein the amount of acetylating agent is 1.3 to 1.4 molar equivalents relative to the 1-palmitoylglycerol.

2. The method of claim 1, wherein the acetylating agent is selected from the group consisting of acetylchloride, acetylbromide and the mixtures thereof.

3. The method of claim 1, wherein the reaction of 1-palmitoylglycerol and the acetylating agent is carried out in a solvent and in the presence of an organic base, wherein the solvent is a non-polar, aprotic solvent.

4. The method of claim 3, wherein the organic base comprises pyridine.

5. The method of claim 3, wherein the non-polar, aprotic solvent comprises one or more of a solvent selected from dichloromethane, acetone, ethyl acetate, and mixtures of any of these.

6. The method of claim 5, wherein the solvent comprises dichloromethane.

7. The method of claim 1, wherein after reacting the 1-palmitoylglycerol with the acetylating agent, water and acid is added to induce a phase separation, and the organic layer is separated and filtered to obtain a filtrate.

8. The method of claim 7, wherein the filtrate is dissolved in a saturated hydrocarbon solvent having 5-7 carbon atoms, and the solution thus obtained is cooled to precipitate crystalline 1-palmitoyl-3-acetylglycerol.

9. The method of claim 8, wherein the crystallization temperature is 0 to 15° C.

10. The method of claim 1 wherein the 1-palmitoylglycerol and 1-palmitoyl-3-acetylglycerol each have the (R) configuration.

11. A method for preparing 1-palmitoyl-2-linoleoyl-3-acetylglycerol comprising the steps of:
   preparing 1-palmitoyl-3-acetylglycerol in accordance with claim 1,
   activating linoleic acid by reacting linoleic acid with pivaloyl chloride in the presence of an organic base to obtain a mixed anhydride;
   reacting the 1-palmitoyl-3-acetylglycerol with the mixed anhydride of linoleic acid in the presence of a catalyst, and
   isolating the 1-palmitoyl-2-linoleoyl-3-acetylglycerol thus obtained.

12. The method of claim 11, wherein the reaction of linoliec acid and pivaloyl chroide is carried out in a non-polar organic solvent in the presence of an organic base.

13. The method of claim 11, wherein the catalyst is 4-dimethylaminopyridine (DMAP).

14. The method of claim 11 wherein the step of isolating the 1-palmitoyl-2-linoleoyl-3-acetylglycerol does not include any purification process using a column chromatography.

15. The method of claim 11, wherein 1-palmitoyl-2-linoleoyl-3-acetylglycerol is obtained in high purity of more than 98% and in high yield of more than 70%.

16. The method of claim 11 wherein the 1-palmitoyl-3-acetylglycerol and the 1-palmitoyl-2-linoleoyl-3-acetylglycerol are each racemic.

17. The method of claim 11 wherein the 1-palmitoyl-3-acetylglycerol and the 1-palmitoyl-2-linoleoyl-3-acetylglycerol each have the (R) configuration.

* * * * *